US009830718B2

(12) United States Patent
Hirai et al.

(10) Patent No.: US 9,830,718 B2
(45) Date of Patent: Nov. 28, 2017

(54) IMAGE PROCESSOR, IMAGE PROCESSING METHOD, AND TREATMENT SYSTEM

(71) Applicant: Kabushiki Kaisha Toshiba, Minato-ku (JP)

(72) Inventors: Ryusuke Hirai, Shinagawa (JP);
Yukinobu Sakata, Kawasaki (JP);
Yasunori Taguchi, Kawasaki (JP);
Tomoyuki Takeguchi, Kawasaki (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 0 days.

(21) Appl. No.: 14/847,630

(22) Filed: Sep. 8, 2015

(65) Prior Publication Data

US 2016/0148401 A1  May 26, 2016

(30) Foreign Application Priority Data

Nov. 26, 2014 (JP) .................................. 2014-239143

(51) Int. Cl.
*G06T 11/00* (2006.01)
*G06T 15/08* (2011.01)
(Continued)

(52) U.S. Cl.
CPC ............ *G06T 11/008* (2013.01); *A61N 5/107* (2013.01); *G06T 7/30* (2017.01); *G06T 15/08* (2013.01);
(Continued)

(58) Field of Classification Search
None
See application file for complete search history.

(56) References Cited

U.S. PATENT DOCUMENTS 4,674,046 A * 6/1987 Ozeki ................. A61B 6/4447
324/312
4,875,165 A * 10/1989 Fencil .................... G06T 7/593
345/424
(Continued)

FOREIGN PATENT DOCUMENTS

JP    2009-34503 A    2/2009
JP    2012-81101 A    4/2012
(Continued)

*Primary Examiner* — Tsung-Yin Tsai
(74) *Attorney, Agent, or Firm* — Oblon, McClelland, Maier & Neustadt, L.L.P.

(57) ABSTRACT

According to some embodiments, an image processor includes an image generator, a region acquirer, and a label applicator. The region acquirer acquires at least one two-dimensional region designated on at least one first perspective image generated from three-dimensional volume data of a target. The label applicator applies a label on at least one first three-dimensional region. The at least one first three-dimensional region is a part of a second three-dimensional region. The second three-dimensional region is defined by the at least one two-dimensional region, a point and a surface which is defined by a set of straight lines between the point and the boundary of the two-dimensional region. The first three-dimensional region is defined to be a first overlapping region where the three-dimensional volume data and the second three-dimensional region overlap.

17 Claims, 12 Drawing Sheets

(51) Int. Cl.
   *G06T 7/30*   (2017.01)
   *A61N 5/10*   (2006.01)
(52) U.S. Cl.
   CPC ...... *A61N 5/103* (2013.01); *A61N 2005/1062* (2013.01); *G06T 2207/10072* (2013.01); *G06T 2207/10116* (2013.01); *G06T 2207/10124* (2013.01); *G06T 2207/30004* (2013.01)

(56) References Cited

U.S. PATENT DOCUMENTS

| | | | | |
|---|---|---|---|---|
| 4,984,160 | A * | 1/1991 | Saint Felix | G06T 11/006 378/62 |
| 5,023,895 | A * | 6/1991 | McCroskey | G01N 23/046 378/10 |
| 6,047,080 | A * | 4/2000 | Chen | G06T 11/006 382/128 |
| 6,823,044 | B2 * | 11/2004 | Rosner | G01N 23/02 378/62 |
| 7,711,087 | B2 * | 5/2010 | Mostafavi | A61B 6/025 378/22 |
| 8,165,365 | B2 | 4/2012 | Bernard et al. | |
| 8,718,347 | B2 * | 5/2014 | Ichihara | A61B 6/032 378/20 |
| 8,787,646 | B2 * | 7/2014 | Schaefer | A61B 6/032 382/131 |
| 2005/0135664 | A1 * | 6/2005 | Kaufhold | G06T 11/006 382/131 |
| 2007/0041491 | A1 * | 2/2007 | Sadakane | A61B 6/589 378/15 |
| 2012/0296193 | A1 * | 11/2012 | Koktzoglou | A61B 5/02007 600/410 |
| 2013/0249903 | A1 | 9/2013 | Isokawa et al. | |
| 2014/0185923 | A1 * | 7/2014 | Chen | G06K 9/00201 382/154 |
| 2015/0193932 | A1 * | 7/2015 | Hashimoto | A61B 6/032 382/132 |

FOREIGN PATENT DOCUMENTS

| | | |
|---|---|---|
| JP | 5400326 B2 | 1/2014 |
| JP | 5416845 B2 | 2/2014 |
| JP | 5536607 B2 | 7/2014 |

* cited by examiner

IMAGE PROCESSOR, IMAGE PROCESSING METHOD, AND TREATMENT SYSTEM

CROSS-REFERENCE TO RELATED APPLICATIONS

This application is based upon and claims the benefit of priority from Japanese Patent Application No. 2014-239143, filed Nov. 26, 2014; the entire contents of which are incorporated herein by reference.

FIELD

Embodiments described herein relate generally to an image processor, an image processing program, an image processing method, and a treatment system.

BACKGROUND

CT (computer tomography) scans an object using particle rays which pass through an object, such as radiation rays, to construct an image within the object. Three-dimensional volume data which are obtained with the CT may be used in understanding a shape or a construction within the object, so that the CT is widely used in non-destructive inspections of the object, medicine, etc. For example, an arbitrary cross-sectional image of the object, or a perspective projection image of the object from an arbitrary viewpoint is reconstructed from the three-dimensional volume data to cause the state within the object to be visualized.

In radiation treatment, image comparison is performed between DRRs (digital reconstructed radiographs) reconstructed from the three-dimensional volume data generated by a device for CT and X-ray images acquired by capturing a patient immediately before the treatment. Alignment between a lesion and a radiation irradiation region is performed based on results of the image comparison. The radiation treatment is a treatment method in which the radiation rays are irradiated onto the lesion of the patient to destruct the tissue of the lesion. Therefore, an occurrence of misalignment between the lesion and the radiation irradiation region causes the tissue of the lesion to remain. To accurately perform the alignment between the lesion and the radiation irradiation region, three-dimensional volume data of the patient are acquired by the CT before the treatment and the position of the lesion is detected three-dimensionally. Moreover, based on the position of the lesion that is detected three-dimensionally, a treatment plan is established. The treatment plan specifies the radiation intensity and the direction of irradiating the radiation rays efficiently to the lesion.

Moreover, in the treatment, when the radiation rays are irradiated in accordance with the treatment plan, it is necessary to align the position of the patient when the treatment plan is established and the position of the patient when the treatment is carried out. Therefore, image comparison is performed between the X-ray images acquired by X-ray capturing immediately before the treatment and a plurality of DRRs reconstructed from the three-dimensional volume data used in the treatment plan, and the DRR which most resembles the X-ray images is searched. Then, the misalignment is calculated between the position of the patient when the treatment plan is established and the position of the patient immediately before the treatment, and a bed on which a patient lies is moved based on the calculated misalignment. This alignment is performed in three-dimensional space, so that the image comparison is performed between each of the X-ray images shot from multiple directions and the DRRs.

The time at which the X-ray images are shot and the time at which the three-dimensional volume data to be a source for the DRRs may differ, causing misalignment in a posture, etc., of the patient. For example, the opening degree of the jaw of the patient may differ, causing misalignment in a joint. Moreover, misalignment may occur since it is likely for deformation to occur in a soft tissue in the body, etc. The misalignment in the joint and the shape may be a factor which adversely affects the image matching. Then, one or both of a region on an image used in the image comparison and a region on an image not used in the image comparison may be set by a user to cause the precision of the alignment to be improved. A region set by the user herein is referred to as ROI (Region of Interest).

The ROI is possibly set by the user in the X-ray images, not in the large number of DRRs that are reconstructed at the time of alignment. However, when the ROI is set in the X-ray images, the ROI needs to be set for each time of treatment in radiation treatment performed over multiple times. On the other hand, if the ROI is set on the three-dimensional volume data, setting the ROI for each time of treatment may be omitted, so it is desirable to set the ROI on the three-dimensional volume data. Moreover, the three-dimensional volume data acquired in the CT show the organs of the patient, making it possible to directly set the lesion or an affected area as the ROI.

Setting the ROI in the three-dimensional volume data may be performed by specifying the ROI on a cross-sectional image to thereby set the ROI in the three-dimensional volume data; however, the ROI needs to be specified on the large number of cross-sectional images to set a three-dimensional region as the ROI, requiring expense in time and effort.

DETAILED DESCRIPTION

Figure 1:
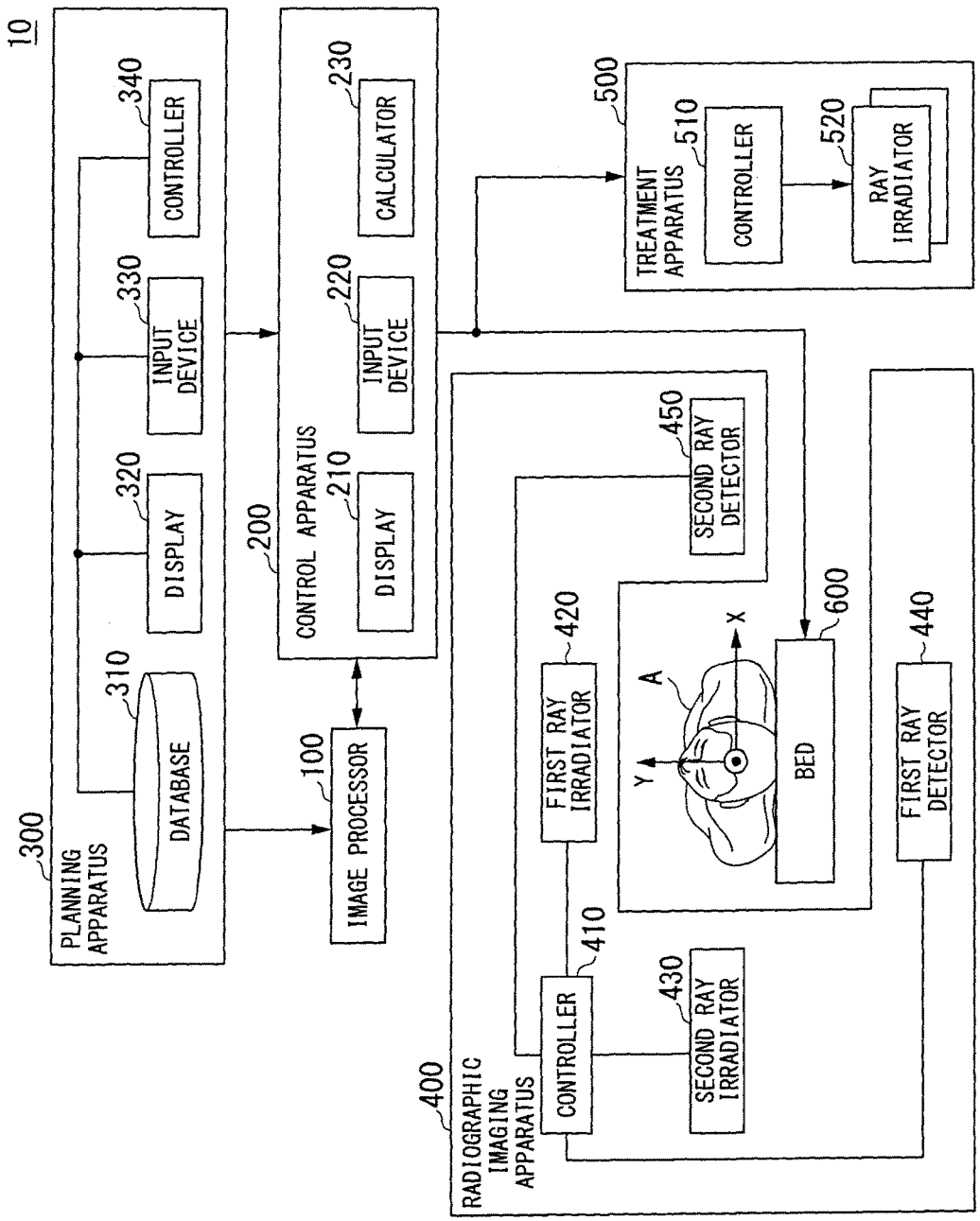
FIG. 1 is a block diagram illustrating a configuration of a treatment system according to a first embodiment.

According to some embodiments, an image processor may include, but is not limited to, an image generator, a region acquirer, and a label applicator. The image generator generates at least one first perspective image from three-dimensional volume data of a target. The region acquirer acquires at least one two-dimensional region designated on the at least one first perspective image. The label applicator applies a label on at least one first three-dimensional region. The at least one first three-dimensional region is a part of a second three-dimensional region. The second three-dimensional region is defined by the at least one two-dimensional region, a point and a surface which is defined by a set of straight line segments between the point and the boundary of the two-dimensional region. The first three-dimensional region is defined to be a first overlapping region where the three-dimensional volume data and the second three-dimensional region overlap each other.

In some cases, the point is a viewpoint for perspective projection to generate the first perspective image.

In some case, the image generator generates the plurality of first perspective images from the three-dimensional volume data using different viewpoints for perspective projection.

In some cases, the image generator generates a first one of the first perspective image. The first one includes a perspective projection of the at least one first three-dimensional region. The image generator makes a perspective projection of the at least one first three-dimensional region to generate the perspective projection region on the first one of the first perspective image. The first one is different from a second one of the first perspective image on which the at least one two-dimensional region is designated.

In some cases, the processor may further include, but is not limited to, a display. The display displays the first one of the first perspective image.

In some cases, the at least one two-dimensional region is a plurality of two-dimensional regions. The label applicator calculates the first three-dimensional region for each of the plurality of two-dimensional regions. The label applicator applies the label on a second overlapping region where the first three-dimensional regions overlap each other.

In some cases, the label applicator applies the label on a set of voxels having voxel values in a range of voxel value. The set of voxels is in the first three-dimensional region.

In some cases, the at least one two-dimensional region includes plural sets of the two-dimensional regions. The label applicator calculates the first three-dimensional region for each two-dimensional region of the plural sets of the two-dimensional regions. The label applicator applies a respective one of the labels on a second overlapping region where the first three-dimensional regions of each set of the two-dimensional regions overlap each other.

In some cases, the respective one of the labels is a respectively different one of the labels.

In some cases, the processor may further include, but is not limited to, an image comparator. The image comparator compares the first perspective image with a second perspective image. The second perspective image is acquired with a radiographic imaging apparatus for capturing the target. The first perspective image is generated by the image generator from the three-dimensional volume data including the at least one first three-dimensional region which is applied with the label by the label applicator.

In some cases, the processor may further include, but is not limited to, a dose calculator. The dose calculator calculates a dose distribution for radiation treatment, based on the three-dimensional volume data on which the label is applied by the label applicator.

In some cases, the processor may further include, but is not limited to, a three-dimensional image generator. The three-dimensional image generator generates a three-dimensional image of the at least one first three-dimensional region.

According to other embodiments, an image processing method may include, but is not limited to, the following processes. At least one first perspective image is generated from three-dimensional volume data of a target by a computer. At least one two-dimensional region designated on the at least one first perspective image is acquired by the computer. A label is applied on at least one first three-dimensional region by the computer. The at least on first three-dimensional region is a part of a second three-dimensional region. The second three-dimensional region is defined by the at least one two-dimensional region, a point and a surface which is defined by a set of straight line segments between the point and the boundary of the two-dimensional region. The first three-dimensional region is defined to be an overlapping region where the three-dimensional volume data and the second three-dimensional region overlap each other.

According to furthermore embodiments, a treatment system may include, but is not limited to, a radiographic imaging apparatus, an image processor, a planning apparatus, and a control apparatus. The planning apparatus stores a three-dimensional volume data of a target and a treatment plan. The image processor may include, but is not limited to, an image generator, a region acquirer, and a label applicator. The image generator generates at least one first perspective image from the three-dimensional volume data. The region acquirer acquires at least one two-dimensional region designated on the at least one first perspective image. The label applicator applies a label on at least one first three-dimensional region. The at least one first three-dimensional region is a part of a second three-dimensional region. The second three-dimensional region is defined by the at least one two-dimensional region, a point and a surface which is defined by a set of straight line segments between the point and the boundary of the two-dimensional region. The first three-dimensional region is defined to be an overlapping region where the three-dimensional volume data and the second three-dimensional region overlap each other. The radiographic imaging apparatus captures at least one second perspective images of the target. The control apparatus generates at least one third perspective image from the three-dimensional volume data with the label applied by the label applicator. The control apparatus performs an image comparison between the at least one second perspective image and the at least one third perspective image. The control apparatus calculates a difference in position of the target between when the three-dimensional volume data, which is used for establishing the treatment plan, is generated by a device for computed tomography and when the at least one second perspective image is captured by the radiographic imaging apparatus.

In some cases, the system may further include, but is not limited to, a bed, and a treatment apparatus. The bed includes a movable mount for the target. The treatment apparatus irradiates the target with radiation. The control apparatus, based on the difference in position, controls the movable mount for irradiation to the target.

According to furthermore embodiments, an image processor may further include, but is not limited to, a processor, and a memory that stores processor-executable instructions that, when executed by the processor, cause the processor to perform the following acts or operations. The processor generates at least one first perspective image from three-dimensional volume data of a target. The processor acquires at least one two-dimensional region designated on the at least one first perspective image. The processor applies a label on at least one first three-dimensional region. The at least one first three-dimensional region is a part of a second three-dimensional region. The second three-dimensional region is defined by the at least one two-dimensional region, a point and a surface which is defined by a set of straight line segments between the point and the boundary of the two-dimensional region. The first three-dimensional region is defined to be a first overlapping region where the three-dimensional volume data and the second three-dimensional region overlap each other.

Various embodiments will be described hereinafter with reference to the accompanied drawings. In the following embodiments, elements to which the same reference numerals are applied perform the same operation and will sometimes not be repeatedly described.

First Embodiment

FIG. 1 is a block diagram illustrating a configuration of a treatment system 10 according to a first embodiment. The treatment system 10 may include, but is not limited to, an image processor 100, a control apparatus 200, a planning apparatus 300, and a radiographic imaging apparatus 400. The treatment system 10 may further include a treatment apparatus 500 and a bed 600. In the treatment system 10, a user such as a technician, a physician, etc., operates the image processor 100, the control apparatus 200, the radiographic imaging apparatus 400, the treatment apparatus 500, and the bed 600 to treat a patient A based on a treatment plan established using the planning apparatus 300. Below, the patient A is referred to as a target.

The planning apparatus 300 establishes a treatment plan with respect to the target A to be subjected to radiotherapy, proton therapy, particle radiotherapy, heavy ion radiotherapy, or the like. The planning apparatus 300 establishes a treatment plan, based on information such as a captured image of the internal form of the target A and operations input by a user. The images used in the planning apparatus 300 are images captured by a radiographic imaging apparatus capable of viewing and capturing the inside of the target A. The radiographic imaging apparatus may be, but is not limited to, an X-ray imaging apparatus, a computed tomography (CT) apparatus, a magnetic resonance imaging (MRI) apparatus, a positron emission tomography (PET) apparatus, or a single photon emission computed tomography (SPECT) apparatus. The images used in the planning apparatus 300 may be either two-dimensional images or three-dimensional images. In the present embodiment, the description will be for the case of images based on volume data collected by an X-ray CT apparatus being used to establish a treatment plan.

The planning apparatus 300 may include, but is not limited to, a database 310, a display 320, an input device 330, and a controller 340. The database 310 has stored the three-dimensional volume data obtained by imaging the target A. The three-dimensional volume data stored in the database 310 may be the voxel data itself obtained by imaging the target A, or may be voxel data after being subjected to correction processing, such as logarithmic conversion, offset correction, sensitivity correction, beam hardening correction, or scattered radiation correction with respect to the data obtained by imaging. In addition to voxel data, the database 310 may store a two-dimensional image reconstructed from voxel data. In the present embodiment, a set of the voxel data in the database 310 will be described for the case of being stored as the three-dimensional volume data (volume data).

The display 320 displays reconstructed images, under the control of the controller 340. The constructed images are digitally reconstructed radiographs (DRR), which are obtained by reconstructing voxel data stored in the database 310. In the first embodiment, the description will be for the case in which images to be used are perspective images of the target A viewed in a predefined direction, that is, a simulated digitally reconstructed radiograph as the reconstructed images. The type of the reconstructed images displayed by the display 320 corresponds to the type of images captured by the radiographic imaging apparatus 400. For example, if the radiographic imaging apparatus 400 is an X-ray imaging apparatus, the reconstructed images displayed on the display 320 are DRR images resulting from simulating an image captured by an X-ray imaging apparatus.

The input device 330 receives instructions from a user, and gives the controller 340 the instructions. The controller 340, based on the instruction, controls the database 310, the display 320 and the input device 330 in the planning apparatus 300. The controller 340 may, for example, be implemented by one or more processors, and executes a program and the instructions to perform control operations based on the program and the instructions. The controller 340, based on information responsive to the reconstructed images and the instructions, stores into the database 310 information indicating a position at which the target A is to be treated.

The radiographic imaging apparatus 400 is an X-ray imaging apparatus or the like, and views and captures an image of the inside of the target A when treatment is performed. The present embodiment will be described for the case of the radiographic imaging apparatus 400 being an X-ray imaging apparatus. The radiographic imaging apparatus 400 may include, but is not limited to, a controller 410, a first ray irradiator 420, a second ray irradiator 430, a first ray detector 440, and a second ray detector 450.

The first ray detector 440 generates a perspective image of the target A, based on an X-ray irradiated from the first ray irradiator 420 that has passed through the target A. The first ray detector 440 may include, but is not limited to, a flat panel detector (FPD). The FPD receives an X-ray that has passed through the target A and converts it to a digital signal. The first ray detector 440 generates the perspective image based on the digital signal obtained from the FPD.

The second ray detector 450 generates another perspective image viewing the target A, based on an X-ray irradiated from the second ray irradiator 430 that has passed through the target A. The second ray detector 450, similar to the first ray detector 440, may include, but is not limited to, an FPD. The second ray detector 450 generates the other perspective image based on the digital signal obtained from the FPD.

The viewing direction in which the first ray detector 440 views the target A differs from that in which the second ray detector 450 views the target A. For example, the first ray irradiator 420, the second ray irradiator 430, the first ray detector 440, and the second ray detector 450 are disposed so that the imaging plane of the FPD of the first ray detector 440 and the imaging plane of the FPD of the second ray detector 450 are mutually perpendicular. The first ray detector 440 and the second ray detector 450 may each have an image intensifier (II) in place of the FPD.

The controller 410 controls the first ray irradiator 420, the second ray irradiator 430, the first ray detector 440, and the second ray detector 450 in the radiographic imaging apparatus 400. The controller 410 may, for example, be implemented by one or more processors, and executes a program to perform control operation based on the program. The controller 410 supplies the control apparatus 200 with a pair of perspective images of the target A that is generated by the first ray detector 440 and the second ray detector 450. Below the perspective images provided from the radiographic imaging apparatus 400 to the control apparatus 200 is referred to as second perspective images.

The image processor 100 reads out the three-dimensional volume data stored in the database 310 of the planning apparatus 300, and sets a region in the three-dimensional volume data as an ROI. The image processor 100 supplies the three-dimensional volume data in which a label is applied based on the ROI set to the control apparatus 200.

Based on the three-dimensional volume data obtained from the image processor 100 and the second perspective images acquired from the radiographic imaging apparatus 400, calculates a difference in position of the target A between when the three-dimensional volume data are acquired and when the second perspective images are captured. The control apparatus 200, based on the difference in positon, controls the bed 600.

The control apparatus 200 may include, but is not limited to, a display 210, an input device 220, and a calculator 230. The display 210 displays an image including the second perspective images and the DRRs that are reconstructed from the three-dimensional volume data. Below, the DRR, which is generated by the calculator 230 from the three-dimensional volume data, is referred to as a third perspective image. The input device 220 receives input of operations from the user and outputs information responsive to the operation input to the calculator 230. The input device 220 includes, for example, a pointing device such as a mouse and a touch panel, and a keyboard or the like. If the input device 220 has a touch panel, the display 210 and the input device 220 may be integrated into a single apparatus.

The calculator 230 generates third perspective images with different viewpoints from the three-dimensional volume data and performs image comparison between the third perspective images and the second perspective images. Based on results of the imaging comparison, the calculator 230 detects the third perspective image which most resembles each one perspective image of the second perspective images. Based on generation conditions at the time of generating the detected third perspective images, the calculator 230 calculates the difference in position of target A between when the three-dimensional volume data is generated by a device for computed tomography and when the second perspective images are captured. Based on the difference in position calculated, the calculator 230 controls the bed 600. A known technique may be applied to calculate the difference in position by the calculator 230.

The treatment apparatus 500 performs treatment that subjects the target A to radiotherapy, proton therapy, particle radiotherapy or heavy ion radiotherapy. The treatment apparatus 500 may include, but is not limited to, a controller 510 and a plurality of ray irradiators 520. The controller 510 controls the plurality of ray irradiators 520 in the treatment apparatus 500. The controller 510 may, for example, be implemented by one or more processors, and executes a program to perform control operations based on the program. The controller 510 makes the ray irradiators 520 operable if the controller 510 detects that the bed 600 has moved the target A based on the difference. Each of the plurality of ray irradiators 520 irradiates toward the target A a radiation beam, a proton beam, a particle beam or a heavy ion beam based on user control when it goes into the movable state. The plurality of ray irradiators 520 are disposed so that the radiation beam, proton beam, particle beam irradiated or heavy ion beam from each of the ray irradiators 520 intersect at one point (isocenter).

The bed 600 may include, but is not limited to, a movable mount upon which the target A rests. The bed 600 moves the movable mount on which the target A rests, based on the difference in position of the target A calculated in the control apparatus 200. This aligns the lesion of the target A determined at the time of treatment planning with the isocenter, and rays for treatment are irradiated form the treatment apparatus 500 to destruct the tissue of the lesion. The movable mount is in the form of a stage, a chair, or the like.

Here, a method of generating the DRR that is used in the treatment system 10 is described. The DRR is an image which is generated for simulating the X-ray image, so that first a capturing model of the X-ray image is described, after which the method of generating the DRR will be described.

The capturing model of the X-ray image is described. In the capturing of the X-ray image, the magnitude of the X-ray energy when the X-rays irradiated toward a subject from an X-ray source pass through the subject to reach the FPD is converted to a pixel value to capturing an X-ray image. In the FPD, X-ray detectors are arranged on a two-dimensional plane and the energy of the X-rays that are detected by each of the X-ray detectors is converted to a pixel value. The energy of the X-rays when the X-rays pass through the subject to reach the FPD is attenuated in response to tissues within the subject, the X-ray image is created from magnitude of energy of the X-ray which has penetrated through a target. The X-ray energy Pi which has just reached at an X-ray detector on each pixel i∈$R^2$ in the X-ray image can be expressed by the Expression (1).

$$P_i = P_0 \exp\{-\oint \mu(l,p)dl\} \tag{1}$$

In Expression (1), $P_0$ is the X-ray energy upon striking the subject, and $\mu(l,p)$ is the linear attenuation coefficient of an object at position l. The linear attenuation coefficient is a value varies in accordance with the X-ray energy P passing through a substance from the beam source. The value obtained by linearly integrating the linear attenuation coefficient of the substance in the path of the X-rays from the beam source up until reaching the X-ray detector disposed at pixel position i is the X-ray energy reaching the X-ray detector. Because the detection characteristics of the X-ray detectors are designed so as to be linear when the logarithm of $P_i$, is taken, an X-ray image is obtained by performing a linear conversion of the signal output from the X-ray detectors to pixel values. That is, the pixel values $T_i$ for each pixel of the X-ray image can be expressed by the Expression (2), in which $\log(P_0)$ is a constant.

$$T_i(P_0) = \log(P_i) = \log(P_0) - \oint \mu(l,P)dl \tag{2}$$

As noted above, each pixel of an X-ray image obtained by X-ray imaging are pixel values in accordance with sum of the products of the linear attenuation coefficient of the target A on the path of the X-ray irradiated from the ray source until reaching the X-ray detectors of the FDP.

Figure 2:
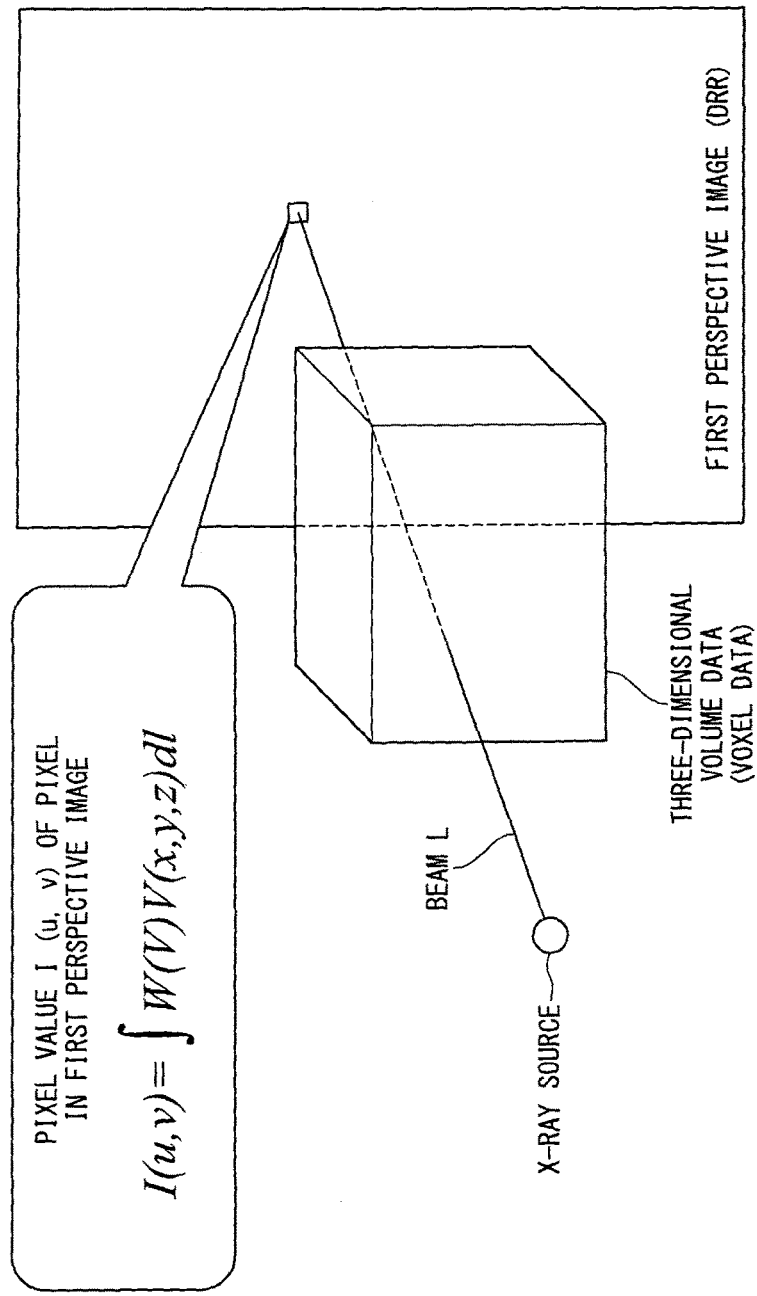
FIG. 2 is a diagram illustrating a process when generating a DRR.

A method of generating the DRR is described. When the target A, which is described with the three-dimensional volume data, for example, is virtually arranged on the bed 600, the DRR is generated by performing a perspective projection from an arbitrary direction. FIG. 2 illustrates the processing when the digitally reconstructed radiograph is generated. The coordinates in the three-dimensional coordinate system with the isocenter as the origin being (x, y, z), the two-dimensional coordinates in the digitally reconstructed radiograph are (u, v). The pixel values I(u, v) of a pixel at the coordinates (u, v) of the digitally reconstructed radiograph are calculated by the Expression (3).

$$I(u,v) = \int W(V) V(x,y,z) dl \quad (3)$$

In Expression (3), V(x, y, z) is the value of the three-dimensional volume data at the coordinates (x, y, z) of the target A virtually disposed on the bed 600. The pixel value I(u, v) is obtained by integrating the values of the three-dimensional volume data on the beam L, as shown in Expression (3). W(V) is a weighting coefficient applied to the values of the three-dimensional volume data. A DRR in which specific values of the three-dimensional volume data are emphasized can be generated by controlling the weighting coefficient W(V). Controlling the weighting coefficient W(V) can be done to emphasis tissue of interest when comparing a DRR and an X-ray image, and to emphasis and improve the visibility of tissue of interest to the user.

The data value V(x, y, z) is a value based on the linear attenuation coefficient of the substance positioned at the location (x, y, z). Given this, if the DRR is generated using the sum of the linear attenuation coefficients of the subject on the path of the beam L, the pixel value of the X-ray image, as shown by Expression (2), also is determined by the sum of the linear attenuation coefficients on the beam, so that the DRR and the X-ray image are similar.

In order to generate a DRR, it is necessary to determine the path of the beam L and the position of the volume data in the target A. When positioning the target A in the treatment system 10, the path of the beam L and the position in the target A for generating the DRR are determined based on the path of the X-rays reaching the FPD in the radiographic imaging apparatus 400 when second perspective images of the target A is captured during treatment.

A reconstructed image other than the DRR includes an MIP (a maximum intensity projection) image. The MIP image, which is called a maximum value projection image, is an image reconstructed from the three-dimensional volume data in the same manner as the DRR. Each of the pixel values of the MIP image is determined from the data value V (x, y, z) on the path of the beam in the same manner as the DRR. The difference thereof from the DRR is that a maximum value of the data values on the path of the beam rather than an integrated value of the data values on the path of the beam is set to be a pixel value.

As described above, a viewpoint and a projection face which specify the path of the beam for the reconstructed image such as the DRR, the MIP image, etc., may be specified to obtain perspective images from a large number of different directions.

Figure 3:
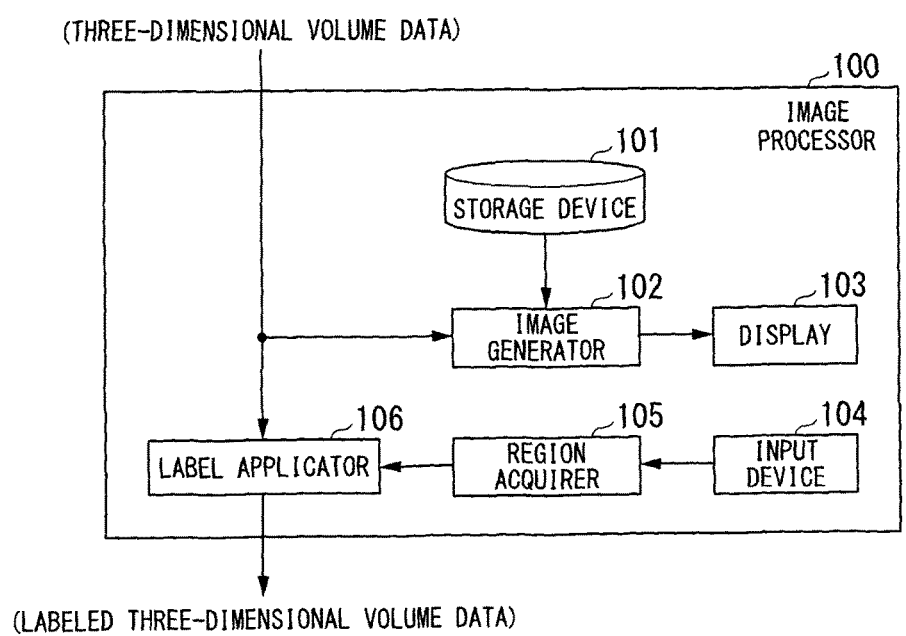
FIG. 3 is a block diagram illustrating a configuration of an image processor according to the first embodiment.

FIG. 3 is a block diagram illustrating a configuration of the image processor 100 according to the first embodiment. As shown in FIG. 3, the image processor 100 may include, but is not limited to, a storage device 101, an image generator 102, a display 103, an input device 104, a region acquirer 105, and a label applicator 106. The storage device 101 stores, in advance, parameters to be used when the image generator 102 generates the first perspective image from the three-dimensional volume data. The parameters stored in the storage device 101 are information including coordinates which determine the projection face and the viewpoint for the three-dimensional volume data. For these parameters, parameters which are determined based on the positional relationship between the first ray irradiator 420 and the first ray detector 440 of the radiographic imaging apparatus 400 and the positional relationship between the second ray irradiator 430 and the second ray detector 450 of the radiographic imaging apparatus 400 may be used, for example.

The image generator 102 reads the three-dimensional volume data of the target A from the database 310 of the planning apparatus 300. Based on the parameters stored in the database 310 and the three-dimensional volume data, the image generator 102 generates the first perspective image by the above-described method. The image generator 102 supplies the generated first perspective image to the display 103. The display 103 displays the first perspective image generated by the image generator 102. The display 103, which is arranged to include an LCD (liquid crystal display), for example, displays the first perspective image such that the user may visualize it.

The input device 104 receives instructions from the user, and gives the region acquirer 105 the instructions. The input device 104 is a keyboard, a mouse, or a pointing device such as a touch pen, etc. Via the input device 104, the user specifies a region on the first perspective images displayed on the display 103. The instructions sent to the region acquirer 105 from the input device 104 include information indicating a region specified by the user. For specifying the region, there are methods including a method of pasting together basic figures such as a quadrilateral, a circle, etc., for example, on the first perspective images displayed in the display 103 to specify a region, a method of handling a range in the first perspective image, over which range the point device traces as a region.

The region acquirer 105 acquires information indicating a two-dimensional region designated by the user on the first perspective image from the input device 104, and supplies the obtained information to the label applicator 106. The label applicator 106 reads the three-dimensional volume data for the target A from the database 310 of the planning apparatus 300. Based on a first three-dimensional region determined by the two-dimensional region designated on the first perspective image and a viewpoint for perspective projection to generate the first perspective image, the label applicator 106 specifies a ROI in the three-dimensional volume data. The first three-dimensional region is a part of a second three-dimensional region. The second three-dimensional region is defined by the two-dimensional region, the viewpoint and a surface which is defined by a set of straight line segments between the viewpoint and the boundary of the two-dimensional region. A shape of the two-dimensional region may be a round or a polygon having more than three edges. The label applicator 106 applies a label to each voxel which makes up the three-dimensional volume data based on the ROI specified in the three-dimensional volume data. The label applicator 106 supplies the three-dimensional volume data including the label to the control apparatus 200.

Figure 4:
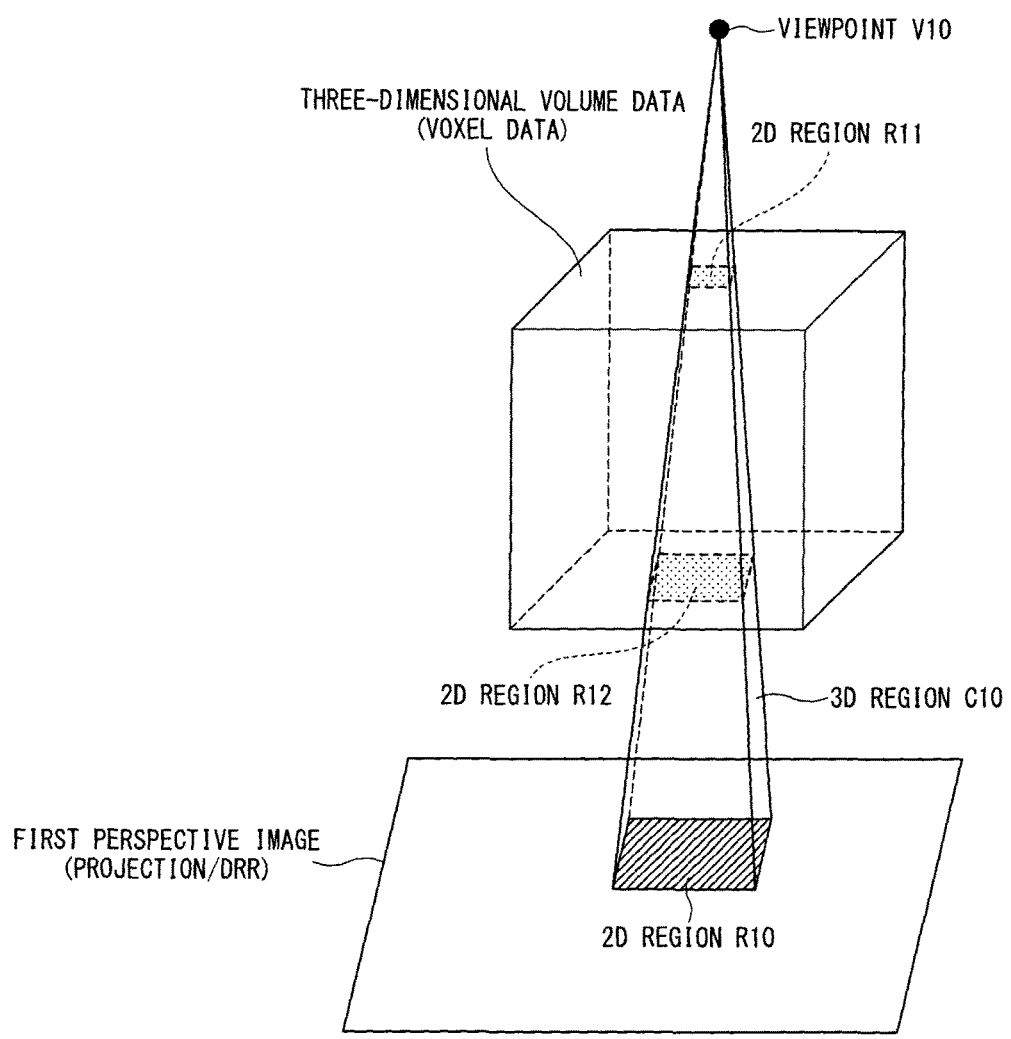
FIG. 4 is a diagram illustrating an overview of an operation performed by a label applicator according to the first embodiment.

FIG. 4 is a diagram illustrating an overview of an operation performed by the label applicator 106 according to the first embodiment. As shown in FIG. 4, when a two-dimensional region R10 of a quadrilateral shape on the first perspective image is designated, the label applicator 106 calculates a second three-dimensional region C10 which connects a region R10 and a viewpoint V10. In this case, the second three-dimensional region C10 is a quadrilateral pyramid. With a face on the viewpoint V10 side being set as a two-dimensional region R11 and a face on the first perspective image side being set as a two-dimensional region R12 out of faces which cross the second three-dimensional region C10 in the three-dimensional volume data, a first three-dimensional region in which the second three-dimensional region C10 and the three-dimensional volume data overlap is a truncated quadrilateral pyramid with the two-dimensional region R11 and the two-dimensional region R12 as base faces. When the two-dimensional region R10 is designated on the first perspective image, a voxel included in the truncated quadrilateral pyramid is specified as the ROI. The label applicator 106 applies a label to the voxels included in the truncated quadrilateral pyramid.

The label applicator 106 may apply the label to the voxel having a CT value within a predetermined range out of the voxels included in the first three-dimensional region. The CT value of the voxel differs in the value in accordance with the tissue of the target A in the voxel position, making it possible to identify the tissue in accordance with the CT value. The characteristics may be used to apply the label only to the voxel having a CT value included within a range of the CT value that indicates a bone out of the voxels included in the designated region, for example.

Figure 5:
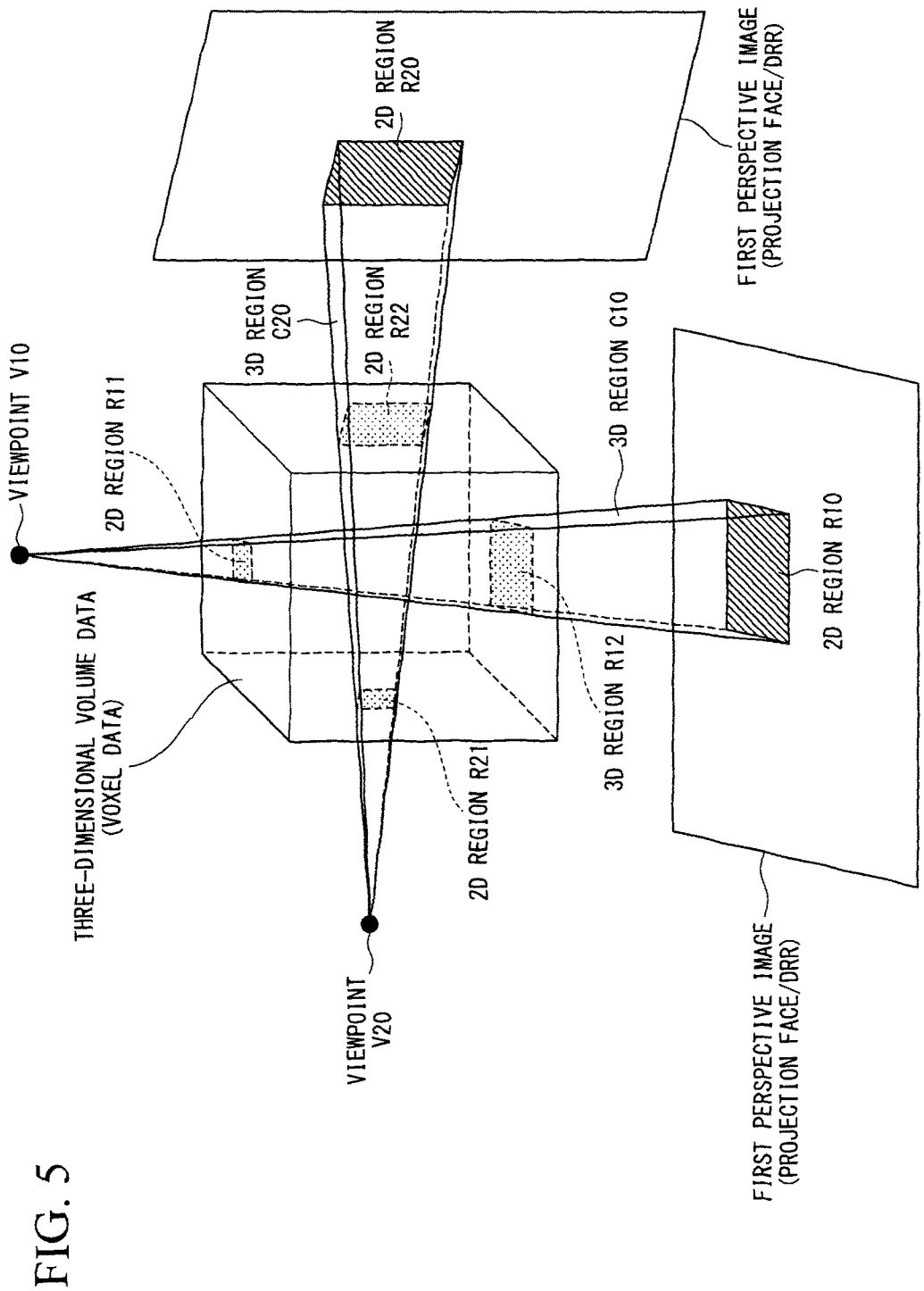
FIG. 5 is a diagram illustrating an overview of a different operation performed by the label applicator according to the first embodiment.

Moreover, instead of designating the two-dimensional region on the first perspective image, the two-dimensional region may be designated respectively in the two first perspective images. FIG. 5 is an overview illustrating a different operation performed by the label applicator 106 according to the first embodiment. In the operation shown, in addition to designating a two-dimensional region R10, a two-dimensional region R20 is designated respectively on two first perspective images. When the two-dimensional regions R10 and R20 are designated respectively on the two first perspective images, the label applicator 106 determines the second three-dimensional region C10 which connects the viewpoint V10 and the two-dimensional region R10 designated on the first perspective image generated based on the viewpoint V10. Moreover, the label applicator 106 determines a second three-dimensional region C20 which connects a viewpoint V20 and the region R20 designated on the first perspective image generated based on the viewpoint V20.

With a face on the viewpoint V20 side being set as a region R21 and a face on the first perspective image side being set as a region R22 out of faces which cross the second three-dimensional region C20 in the three-dimensional volume data, a first three-dimensional region in which the second three-dimensional region C20 and the three-dimensional volume data overlap is a truncated quadrilateral pyramid with the region R21 and the regions R22 as base faces. The label applicator 106 applies a label to the voxel included in the region in which the first three-dimensional region C10 and the C20 overlap in the three-dimensional volume data.

Figure 6:
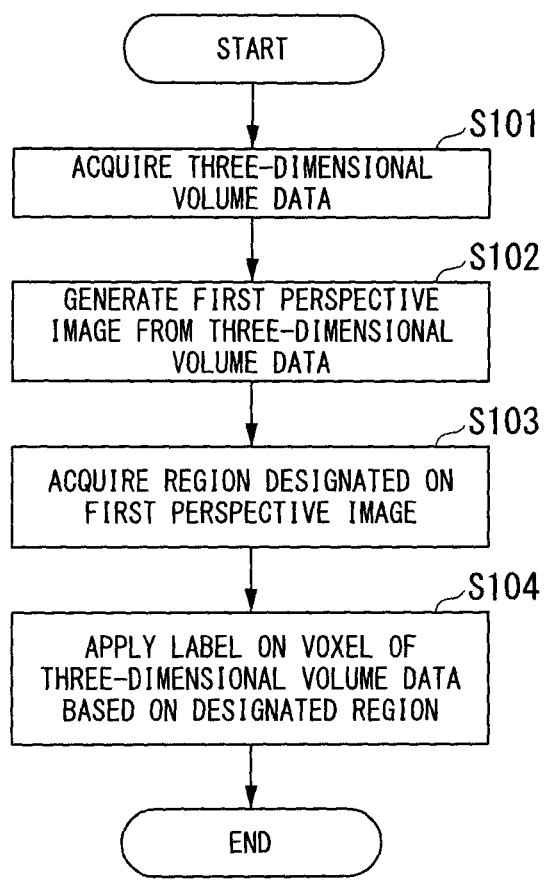
FIG. 6 is a flowchart illustrating a process of label application performed by the image processor according to the first embodiment.

FIG. 6 is a flowchart illustrating a process of label application performed by the image processor 100 according to the first embodiment. When the process is started in the imaging processor 100, the image generator 102 and the label applicator 106 acquire the three-dimensional volume data from the database 310 of the planning apparatus 300 (step S101). Based on the parameters being stored in the storage device 101 and the three-dimensional volume data, the image generator 102 generates at least one first perspective image (step S102). The first perspective image generated by the image generator 102 is displayed in the display 103.

The region acquirer 105 acquires, via the input device 104, information indicating a two-dimensional region designated by the user on the first perspective image displayed in the display 103 (step S103). The label applicator 106 applies a label to each of the voxels corresponding to the first three-dimensional region determined by the information in the three-dimensional volume data based on the information obtained in the region acquirer 105 (step S104). The label applicator 106 sends the three-dimensional volume data which include a voxel on which the label is applied to the control apparatus 200 (step S105), and completes the process.

The image processor 100 which performs the above-described process is used to designate a region of interest in the first perspective image by the user to apply a label on a first three-dimensional region in which overlap the three-dimensional volume data and a second three-dimensional region determined by the designated region on the first perspective image and a viewpoint for perspective projection to generate the first perspective image, making it possible to easily set a region of interest (ROI) in the three-dimensional volume data.

Upon obtaining information indicating a two-dimensional region designated on the first perspective image by the region acquirer 105, the image generator 102 may determine a second three-dimensional region based on the information to generate a first perspective image in which is superimposed a region included in the second three-dimensional region. For example, in an example shown in FIG. 5, when the two-dimensional region R10 is designated, the image generator 102 may generate the first perspective image in which is superimposed a region corresponding to the second three-dimensional region C10 on the first perspective image generated based on the viewpoint V20. In this way, a region corresponding to a second three-dimensional region based on a first one of first perspective images may be indicated on a second one of the first perspective images to visualize the region corresponding to the second three-dimensional region determined with a two-dimensional region designated by the user on the first one of the first perspective image. In this way, the user may easily designate the two-dimensional region on the multiple first perspective images.

Moreover, in examples shown in FIG. 4 and FIG. 5, a case is shown of designating a region for each of one or two first perspective images. However, when the image generator 102 generates at least three first perspective images and the user designates a two-dimensional region on each of the first perspective images, the label applicator 106 applies a label to a voxel of a three-dimensional region in which at least two first three-dimensional regions overlap in the three-dimensional volume data. Furthermore, in this case, the label applicator 106 applies a label to a voxel of a region in which all first three-dimensional regions overlap each other in the three-dimensional volume data.

Furthermore, the label applicator 106 may apply a label on a set of voxels, which have voxel values in a range of voxel value, included the first three-dimensional region in the three-dimensional volume data. When the CT value is set to be a voxel value, an internal tissue may be designated based on the CT value, so that a label may be applied on the voxel having a specific range of CT value to select the internal tissue to apply the label. The internal issue which may be specified based on the CT value includes a bone, a blood vessel, etc., for example.

Second Embodiment

Figure 7:
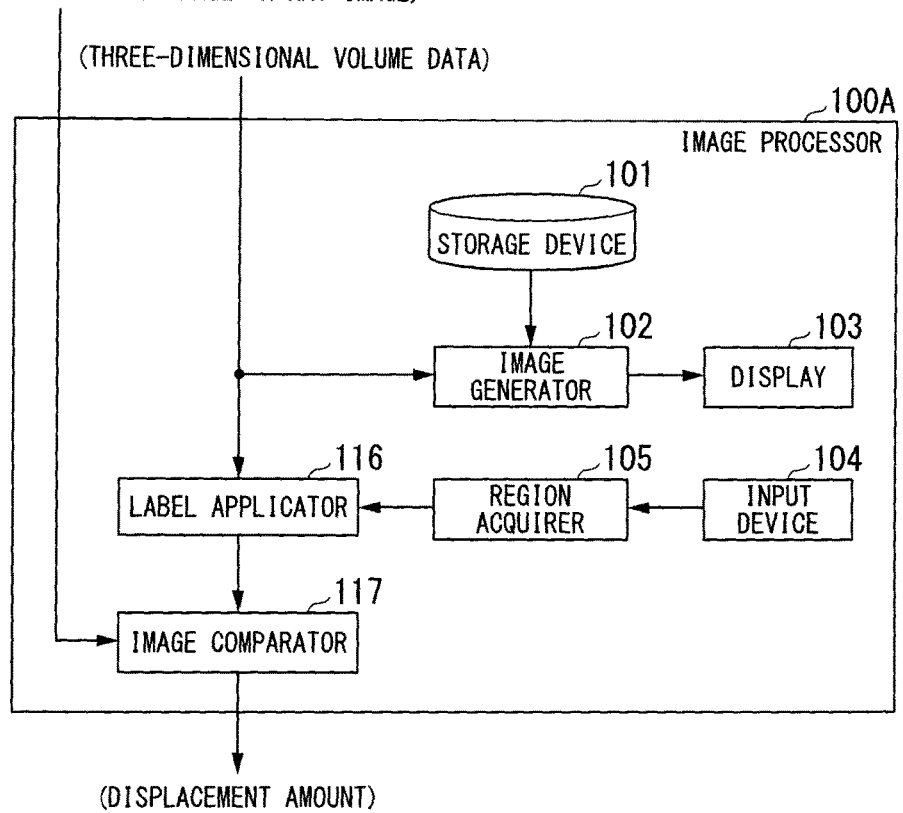
FIG. 7 is a block diagram illustrating a configuration of the image processor according to a second embodiment.

The image processor according to a second embodiment is used in a treatment system 10 (FIG. 1) in the same manner to the image processor 100 according to the first embodiment (FIG. 3). FIG. 7 is a block diagram illustrating a configuration of an image processor 100A according to the second embodiment. As shown in FIG. 7, the image processor 100A may include, but is not limited to, the storage device 101, the image generator 102, the display 103, the input device 104, the region acquirer 105, a label applicator 116, and an image comparator 117. The image processor 100A is different from the image processor 100 of the first embodiment in that it includes the label applicator 116 instead of the label applicator 106 and that it includes the image comparator 117.

In the same manner as the label applicator 106, the label applicator 116 applies a label to a voxel included in three-dimensional volume data based on a two-dimensional region specified by a user on the first perspective image. The label applicator 116 applies one or multiple types of labels on the voxel.

The image comparator 117 obtains the second perspective images which are captured by the radiographic imaging apparatus 400. The image comparator 117 calculates the similarity between the second perspective images and each of the multiple first perspective images generated from the three-dimensional volume data in which the label is applied. Based on the calculated similarity, the image comparator 117 detects a first perspective image which most resembles the second perspective images out of the multiple first perspective images. Based on a position of the three-dimensional volume data of the target A when the detected first perspective images are generated, the image comparator 117 calculates a difference in position of the target A when the detected first perspective images are generated from the three-dimensional volume data of the target A and when the second perspective images are captured by the radiographic imaging apparatus 400. The image comparator 117 supplies the difference in position to the control apparatus 200. The control apparatus 200 controls the bed 600 based on the difference in position calculated by the image comparator 117.

As described above, alignment in which is aligned a difference between the position of the three-dimensional volume data of the target A used to specified the treatment plan and the position of target A when captured by radiographic imaging apparatus 400 for treatment is performed based on results of image comparison between the first perspective images (DRRs) and the second perspective images (X-ray images). This alignment is a process performed in a three-dimensional space, so that second perspective images are captured from at least two mutually different directions.

Figure 8:
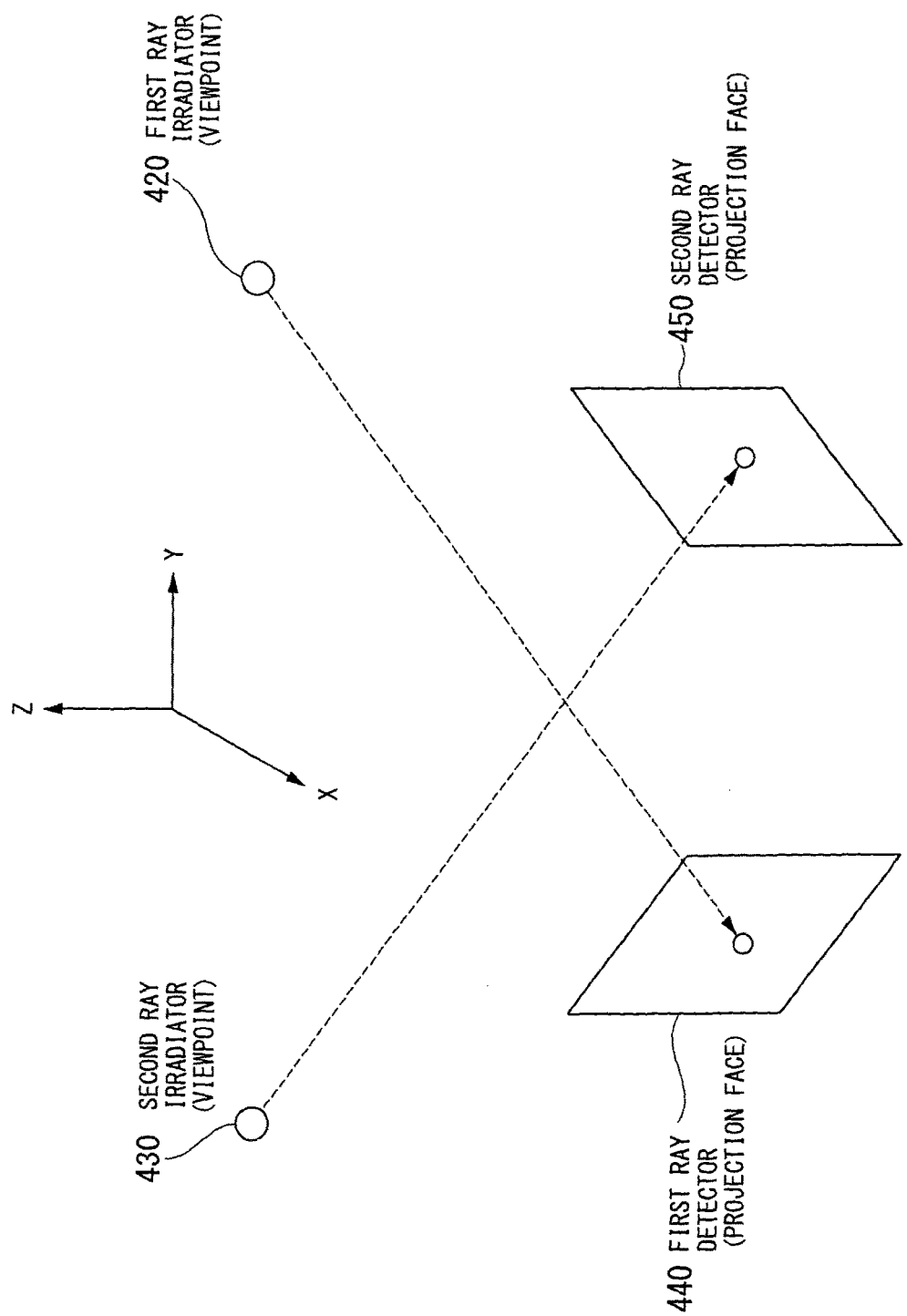
FIG. 8 is a diagram illustrating a positional relationship between first and second ray source devices and first and second imaging devices in a radiographic imaging apparatus which shoots a target A from two different directions.

FIG. 8 is a diagram illustrating a positional relationship between first and second ray irradiators and first and second ray detectors in the radiographic imaging apparatus 400 which captures the target A from two different directions. As shown in FIG. 8, the first ray detector 440 and the second ray detector 450 forming a pair with each of the first ray irradiator 420 and the second ray irradiator 430 are included in the radiographic imaging apparatus 400. The first ray detector 440 and the second ray detector 450 that correspond to a projection face when the second perspective image is generated include an FPD as described above. X-rays output from the first ray irradiator 420 pass through the inside of the target A to reach the first ray detector 440. The first ray detector 440 generates a second perspective image based on the energy of the X-rays which passed through the target A. Similarly, the X-rays output from the second ray irradiator 430 passes through the inside of the target A to reach the second ray detector 450. The second ray detector 450 generates another second perspective image based on the energy of the X-rays which passed through the target A.

In the radiographic imaging apparatus 400, calibration of capturing position is performed for a set of the first ray irradiator 420 and the first ray detector 440 and a set of the second ray irradiator 430 and the second ray detector 450 that image each of the second perspective images. A perspective projection matrix for performing a coordinate transformation between a three-dimensional space coordinate system defined in the radiographic imaging apparatus 400 and a projection face in the first ray detector 440 and the second ray detector 450 is defined in advance.

In this way, when the radiographic imaging apparatus 400 is calibrated, the positional relationship between the projection face and the ray source of the X-rays, or, in other words, the positional relationship between the first ray irradiator 420, the second ray irradiator 430, the first ray detector 440, and the second ray detector 450 is known. In this case, in the image processor 100, a path of a light ray line l used for generating the first perspective image is determined with the position of the ray source of the X-rays as a viewpoint for perspective projection and the detection face of the FPD as the projection face.

As described above, specifying the viewpoint and the projection face when the first perspective images are generated causes the first perspective images and the second perspective images to resemble the most when the position of the target A at the time of obtaining the three-dimensional volume data with a CT apparatus, etc., matches the position of the target A at the time of capturing the second perspective images by the radiographic imaging apparatus 400. The parameters for generating the first perspective images are specified based on the radiographic imaging apparatus 400 which captures the second perspective images to lead to the advantage that image comparison between the first perspective images and the second perspective images is facilitated.

The label applicator 116 applies a label on the voxel which is included in the first three-dimensional region, which is a part of a second three-dimensional region determined by the viewpoint and the two-dimensional region designated on the projection face (second perspective image) shown in FIG. 8. The first three-dimensional region is defined to be an overlapping region where the three-dimensional volume data and the second three-dimensional region overlap. Then, the voxel in which the label is applied may be limited to voxels on which the same label is applied. For example, the voxel on which the label is applied may be selected based on information added to the three-dimensional volume data at the time of treatment planning.

For example, in the treatment plan of the radiation treatment, the irradiation direction and the irradiation intensity of a radiation ray beam is determined. Here, a CTV (clinical target volume) which indicates a range of voxel value for an irradiation target, a PRV (planning organ at risk volume) which indicates another range of voxel value for avoiding the irradiation, etc. are set. The PRV is set for a normal organ, which should not be irradiated. With respect to the voxel in which the label is applied, a label may be applied to the voxel set to the CTV or the PRV in the treatment plan out of the voxels in the second three-dimensional region determined by the two-dimensional region on the first perspective image.

Moreover, the image generator 102 may generate an image in which is superimposed a region of the CTV or the PRV that is specified in the treatment plan on the first perspective image. In this way, the user may designate a two-dimensional region based on the first perspective image in which is superimposed the CTV or the PRV that is displayed in the display 103, facilitating the two-dimensional region to be designated.

Here, the type of a label applied by the label applicator 116 is described. As the type of the label, a calculation region label and a non-calculation region label may be specified, for example. The calculation region label is a label which is applied on the voxel when a region is designated such that the CTV and PRV which are specified in the treatment plan are included. The non-calculation region label is a label which is applied on the voxel when a region is designated as what is to be excluded from similarity calculation in the image comparison. A label may be expressed with a numerical value. For example, a small numerical value is assigned to the non-calculation region label, while a large numerical value is assigned to the calculation region label. Selection on which label is to be assigned to the voxel is performed when the user designates a region on the first perspective image.

The image comparator 117 calculates the similarity between the multiple first and second perspective images and detects the first perspective images with the highest similarity to the second perspective images. The image comparator 117 calculates the position of the target A from the parameters used when generating the detected first perspective images with the highest similarity and calculates a difference in position of the target between the calculated position of the target A and the position of the target A at the time of capturing the second perspective image. The image comparator 117 supplies the difference to the control apparatus 200. The control apparatus 200 controls the bed 600 based on the difference calculated by the image comparator 117 and aligns the isocenter with the position of the lesion of the target A.

The image comparator 117 calculates the similarity E using the Expression (4), for example. The similarity E calculated in the Expression (4) shows that the smaller the value higher the similarity. In the Expression (4), i is a positional vector which indicates a pixel position in the first perspective image and the second perspective image. Ω is a set of all of the pixel positions in the first perspective image and the second perspective image. $w_i$ is a weight on a pixel i and the higher the importance of the pixel i in the image comparison, the higher the value. W, which is a total sum of the weight $w_i$, is calculated in Expression (5). I(i) is a pixel value of the pixel i in the first perspective image. T(i) is a pixel value of the pixel i in the second perspective image.

$$E = \sum_{i \in \Omega} \left[ \frac{w_i}{W} \{I(i) - T(i)\}^2 \right] \quad (4)$$

$$W = \sum_{i \in \Omega} w_i \quad (5)$$

When there is a voxel on which a calculation region label is applied on a light ray line used when generating a pixel i of the first perspective image, for example, 1 is assigned thereto, otherwise 0 is assigned thereto. Moreover, when three types of labels of the calculation region label, no label, and the non-calculation region label are applied on the voxel of the three-dimensional volume data, the weight is assigned such that the value decreases in the order of the calculation region label, no label, and the non-calculation region label. For example, 1 is assigned to "the calculation region label", 0.5 is assigned to "the no label", and 0 is assigned to "the non-calculation region label". When the label is applied with a numerical value which meets the above-described conditions, the value thereof may be used as the weight $w_i$. Moreover, when multiple types of labels are applied on the voxel which is positioned on the light ray line when the first perspective image is generated, the highest weight of weights corresponding to the labels may be used.

A user may designate a two-dimensional region on the first perspective images generated from the three-dimensional volume data using an image processor 100A according to the second embodiment to set a region of interest (ROI) on the three-dimensional volume data. Moreover, the image comparison based on the region of interest set on the three-dimensional volume data may be performed to calculate the difference in position of the target A that focuses on the region of interest and perform alignment which is suitable for radiation treatment.

While the image processor 100A and the control apparatus 200 have been described as different apparatuses in the second embodiment, the image processor 100A and the control apparatus 200 may be arranged as one apparatus. For example, the control apparatus 200 may include an element of the image processor 100A, and supply a difference in position calculated by the image comparator 117 to the calculator 230.

Third Embodiment

Figure 9:
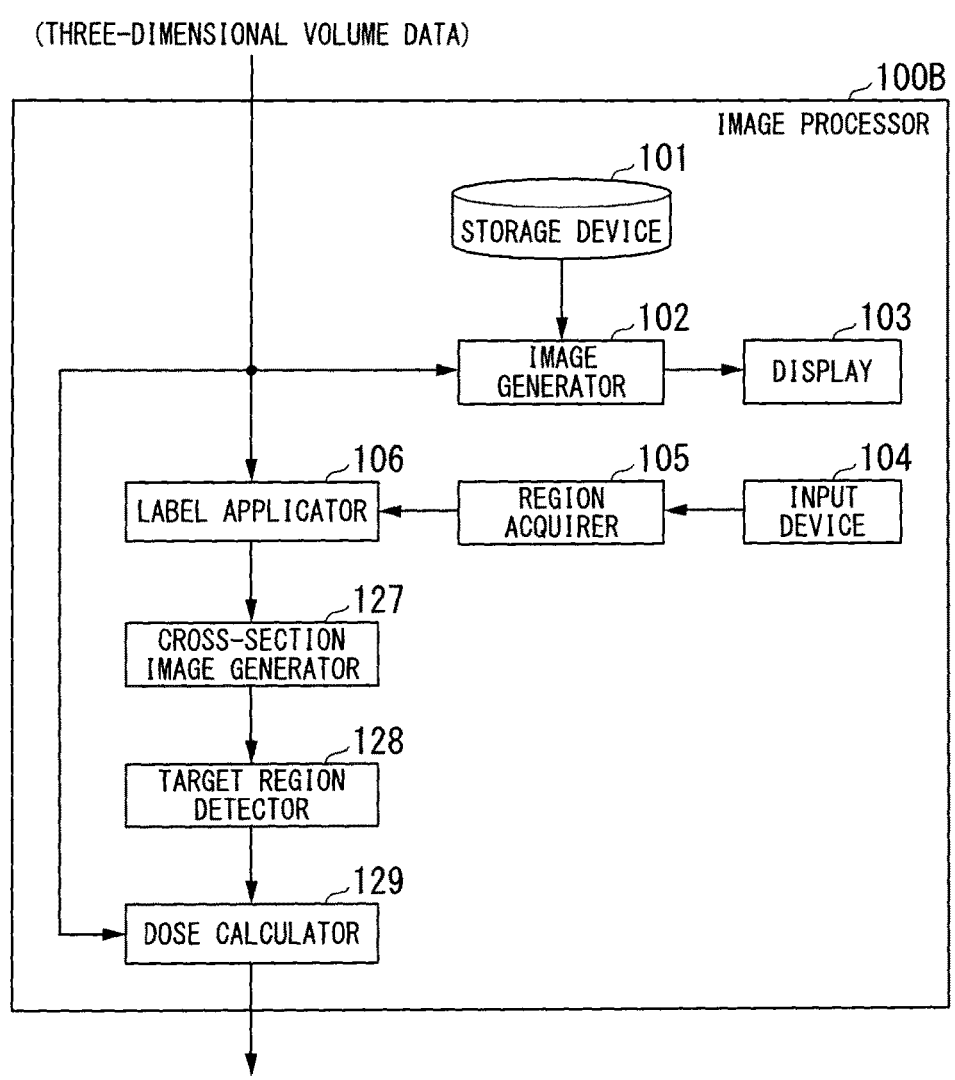
FIG. 9 is a block diagram illustrating a configuration of the image processor according to a third embodiment.

FIG. 9 is a block diagram illustrating a configuration of an image processor 100B according to a third embodiment. As shown, the image processor 100B may include, but is not limited to, the storage device 101, the image generator 102, the display 103, the input device 104, the region acquirer 105, the label applicator 106, a cross-section image generator 127, a target region detector 128, and a dose calculator 129. The image processor 100B is different from the image processor 100 according to the first embodiment in that it further includes the cross-section image generator 127, the target region detector 128, and the dose calculator 129.

The cross-section image generator 127 generates multiple cross-sectional images for a range in which is included a voxel on which is applied a label by the label applicator 106 out of the voxels included in the three-dimensional volume data. The cross-section image generator 127 supplies the cross-sectional images to the target region detector 128. The target region detector 128 performs a region division on each of the multiple cross-sectional images obtained from the cross-section image generator 127.

The target region detector 128 detects a region corresponding to a tumor of a lesion out of the divided region as a target region and specifies a contour of the tumor on the multiple cross-sectional images. The target region detector 128 further applies a label on the voxel corresponding to the target region in the three-dimensional volume data. The label applied by the target region detector 128 is a label which differs from the label applied by the label applicator 106.

The dose calculator 129 performs a dose distribution calculation with the voxel on which the label is applied by the target region detector 128 as the tumor to determine the treatment plan. When the image processor 100B includes the label applicator 116 instead of the label applicator 106, the dose calculator 129 may determine the treatment plan based on the CTV and PRV labels applied by the label applicator 116. For example, the dose calculator 129 inputs the three-dimensional volume data on which the CTV and PRV labels are applied, and determine the intensity and the irradiation direction, etc., of the radiation beam based on the shape and the position of the CTV and the positional relationship between the CTV and the PRV. Moreover, the dose calculator 129 performs dose distribution calculation using the three-dimensional volume data to determine an appropriate treatment plan.

Figure 10:
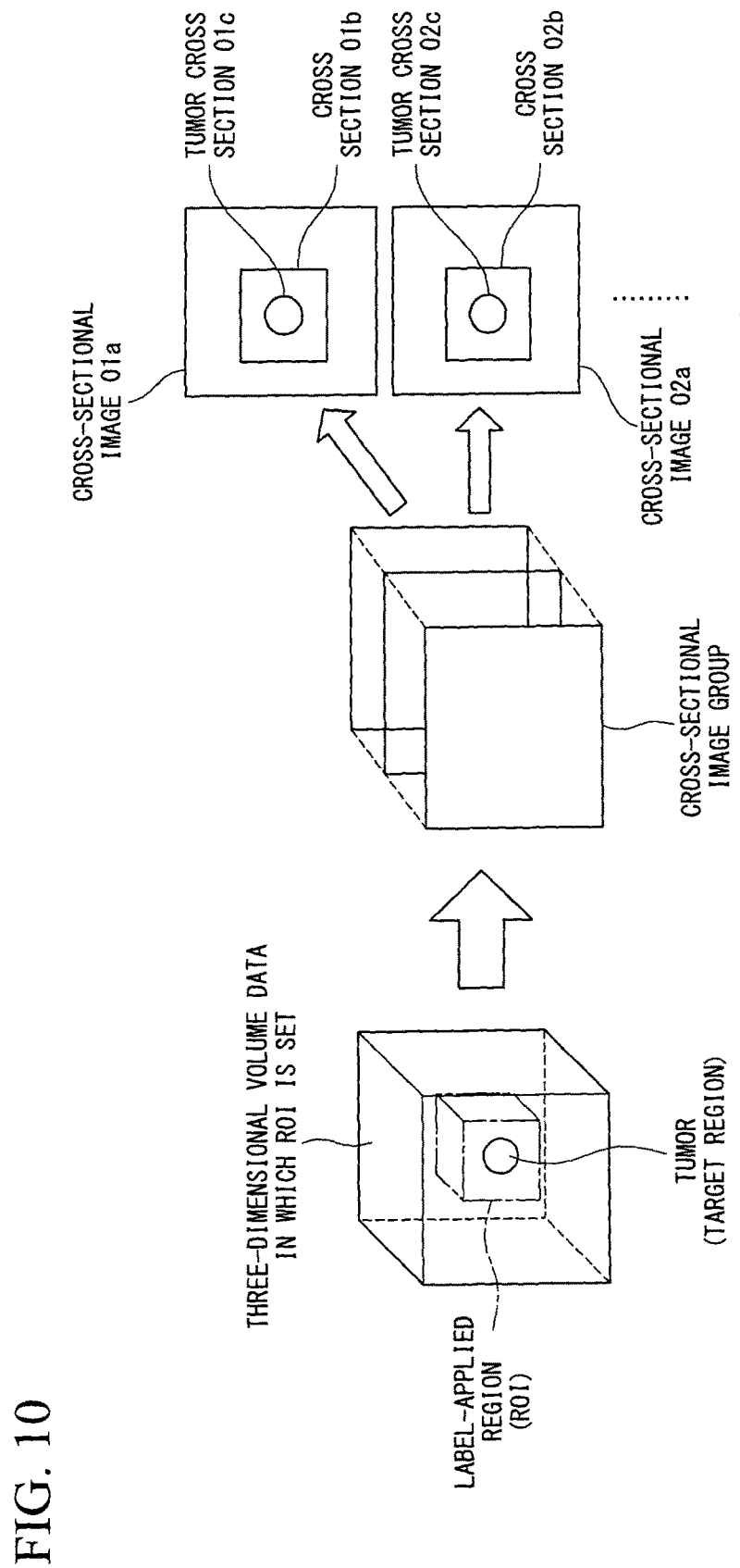
FIG. 10 is a diagram illustrating an overview of a process performed by the image processor.

FIG. 10 is a diagram illustrating an overview of a process performed by the image processor 100B. The three-dimensional volume data in which the ROI is set by the label applicator 106 are generated. The ROI is a cross region in which multiple second three-dimensional regions determined by two-dimensional region on the first perspective images overlap with the three-dimensional volume data. A label is applied on voxels included in the cross region in which the ROI is set. Moreover, a tumor to be the CTV that is a target of irradiation of the radiation in treatment is included in the ROI.

The cross-section image generator 127 generates three-dimensional volume data from a group of cross-sectional images including multiple cross-sectional images when the three-dimensional volume data are cut along multiple faces which are parallel in a predetermined direction. Each of the pixel values in the respective cross-sectional images is acquired from the voxel value of the voxel corresponding to the pixel. The cross-section image generator 127 supplies a cross-sectional image including a pixel corresponding to the voxel on which the label is applied out of the cross-sectional images generated to the target region detector 128.

For each of the multiple cross-sectional images acquired from the cross-section image generator 127, the target region detector 128 performs region division on a region which includes a pixel on which the label is applied in the cross-sectional image. The target region detector 128 specifies a partial region corresponding to a tumor out of multiple partial regions acquired by performing the region division to detect the contour of the tumor. For example, in FIG. 10, a cross-sectional image 01*a* includes a cross-section 01*b*, which is a cross section of a first three-dimensional region as the ROI, on which region the label is applied; the cross-section 01*b* includes a tumor cross-section 01*c*, which is a cross section of the tumor. Acquiring contour information, which indicates the contour of a tumor cross section, in all cross-sectional images including the ROI out of the cross-sectional image group, makes it possible to acquire the contour of the tumor in the three-dimensional volume data.

The region division on the cross section of the first three-dimensional region in the cross-sectional images is performed by the target region detector 128 applying a known method of region division on a three-dimensional region cross-section. For example, as a method of region division, a K-Means method in which a division into two classes is performed in accordance with a characteristic amount of each pixel may be used. For the characteristic amount in the K-Means method, the pixel value may be used. Moreover, a Snake method in which a border of a closed region in an estimated cross-section may be used. As other methods of region division, a Level Set method, a Graph Cut method, etc., may be used.

In the target region detector 128, when multiple closed regions are detected in the cross-section of the first three-dimensional region as a result of the region division, a closed region with a largest area out of the multiple closed regions may be detected as a target region corresponding to the tumor. Moreover, when the multiple closed regions are detected in the cross-section of the first three-dimensional region, the target region detector 128 may select any thereof based on a voxel value (CT value) of a voxel corresponding to each of the closed regions. The target region detector 128 detects the selected closed region as a target region corresponding to the tumor. Moreover, when the closed region is not detected in the cross-section of the first three-dimensional region, the target region detector 128 may output a message notifying the user that setting of the ROI on the tumor can be inappropriate.

The user designates at least one two-dimensional region on the first perspective images generated from the three-dimensional volume data using the image processor 100B according to the third embodiment may be used to set a region of interest (ROI) in the three-dimensional volume data. Moreover, based on the cross section image of the ROI in the three-dimensional volume data, the contour of the tumor of the lesion may be specified and a suitable treatment plan may be determined.

In the same manner as the image processors according to the first and the second embodiments, the image processor 100B according to the third embodiment may be applied to a treatment system. In this case, the image processor 100B may apply a label different from the ROI on a voxel corresponding to a tumor specified as a target region.

Fourth Embodiment

Figure 11:
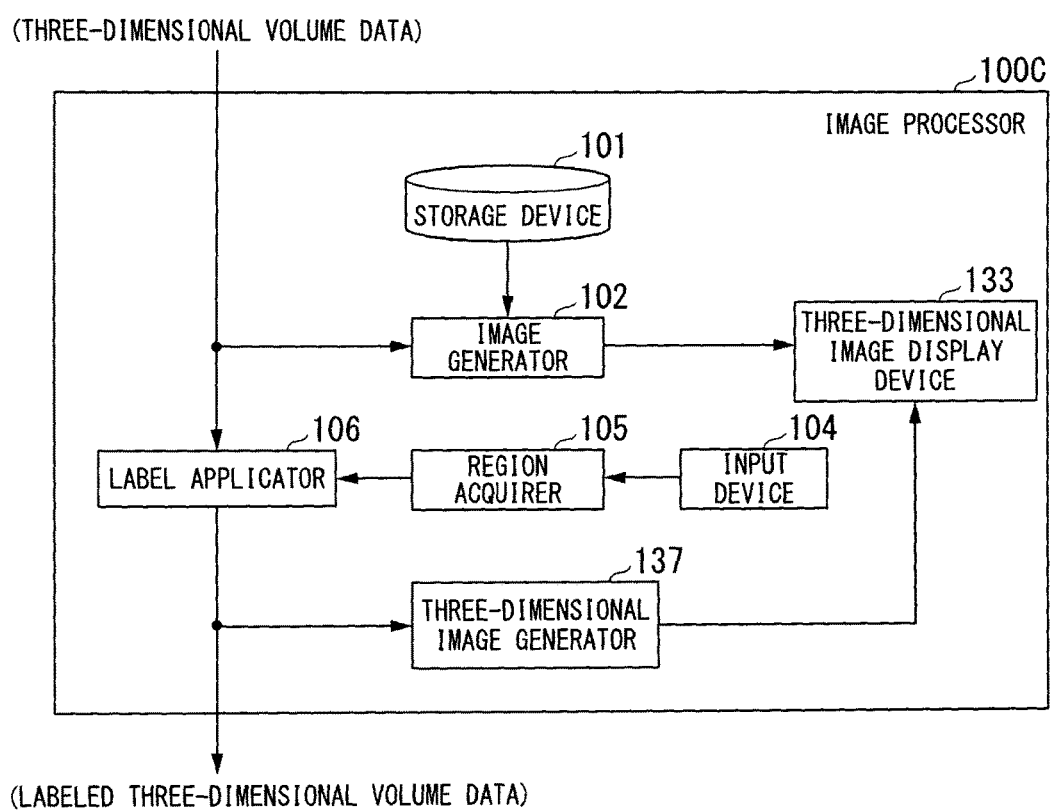
FIG. 11 is a block diagram illustrating a configuration of the image processor according to a fourth embodiment.

The image processor according to the fourth embodiment is used in the treatment system 10 (FIG. 1) in the same manner as the image processor 100 (FIG. 3) according to the first embodiment. FIG. 11 is a block diagram illustrating a configuration of an image processor 100C according to the fourth embodiment. As shown in FIG. 11, the image processor 100C may include, but is not limited to, the storage device 101, the image generator 102, a three-dimensional image display device 133, the input device 104, the region acquirer 105, the label applicator 106, and a three-dimensional image generator 137. The image processor 100C differs from the image processor 100 according to the first embodiment in that it includes the three-dimensional image display device 133 in lieu of the display 103 and it includes the three-dimensional image display device 133.

The three-dimensional image display device 133 includes a display apparatus which may provide a stereoscopic display of an image. The display apparatus which may provide the stereoscopic display is a display apparatus in which, for example, a user wears special glasses, etc., and sees a display face of the display apparatus through the glasses to make stereoscopic views possible. Alternatively, a display apparatus included in the three-dimensional image display device 133 may be a display apparatus which makes stereoscopic views possible without using the special glasses. The three-dimensional image display device 133 displays, as a planar image, the first perspective images generated by the image generator 102, and also an image which makes stereoscopic views possible.

The three-dimensional image generator 137 acquires three-dimensional data on which a label is applied by the label applicator 106 and generates, as a three-dimensional image, a parallax image for stereoscopic views based on the three-dimensional data. The three-dimensional image generator 137 supplies a three-dimensional image to the three-dimensional image display device 133 and causes the three-dimensional image to be displayed on the three-dimensional image display device 133. Using the three-dimensional volume rendering method, the three-dimensional image generator 137 generates images for different viewpoints corresponding to right and left eyes to generate the parallax image.

As a method of generating an image from the three-dimensional volume data, there is a volume rendering method. In the volume rendering method, non-opacity is given to a CT value displayed on an image, while opacity is assigned to a CT value not displayed on the image. Thereafter, rendering is performed by shadowing and coloring in which transmission and reflection of the light ray lines when viewed from a specific viewpoint are performed to generate an image. Unlike the DRR, the MIP image, and the cross-sectional image, rendering may be performed in this way to acquire an image closer to the actual state.

In rendering, even when voxels have the same CT value, different colors may be assigned different colors to the voxel on which a label is applied and to the voxel on which a label is not applied to specify a region on which the label is applied in an image obtained by rendering.

Figure 12:
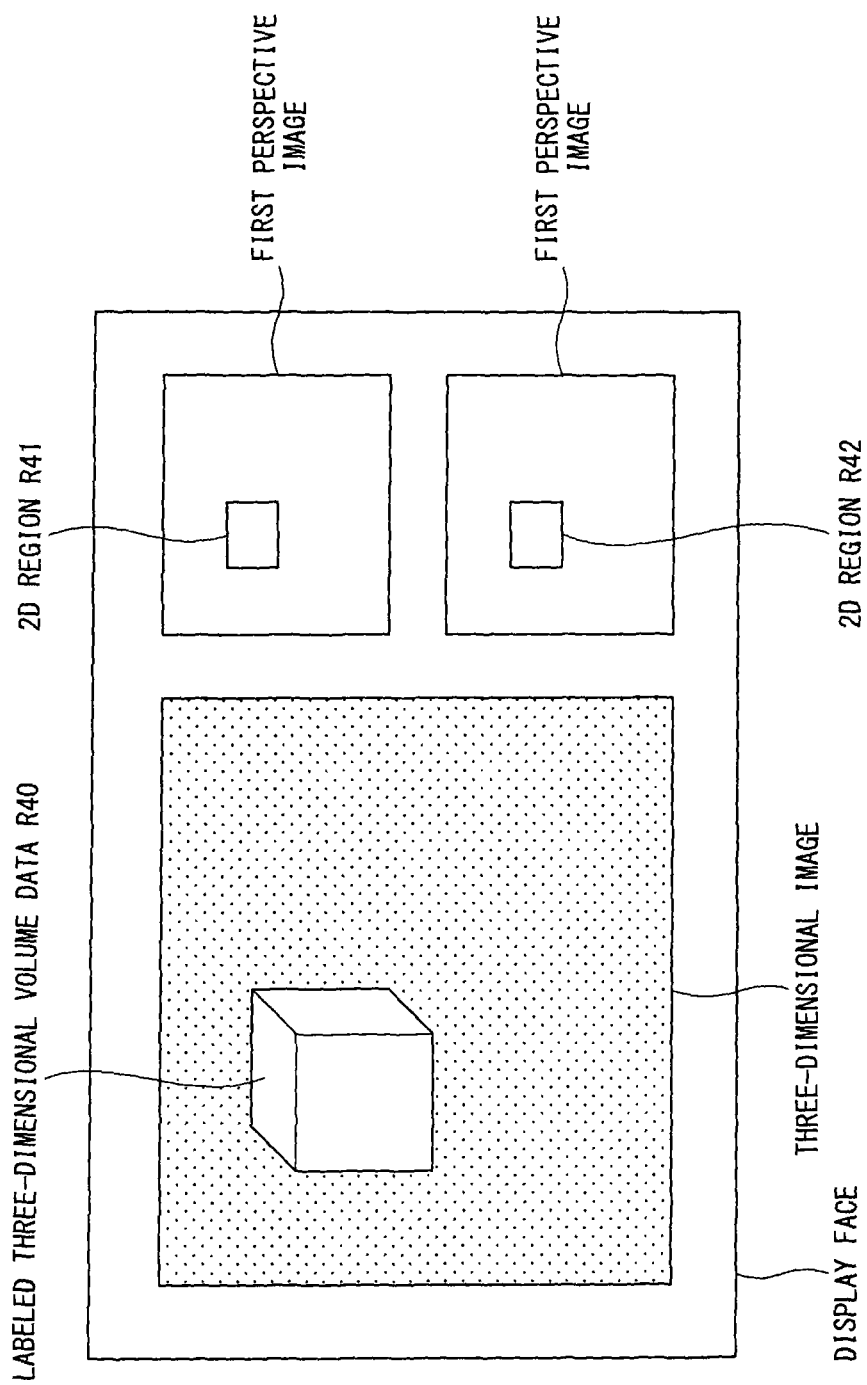
FIG. 12 is an exemplary display of an image in the image processor.

FIG. 12 is a diagram illustrating an exemplary display of an image in an image processor 100C. As shown in FIG. 12, a three-dimensional image generated by the three-dimensional image generator 137 and two first perspective images generated by the image generator 102 are shown on a display face of the three-dimensional image display device 133. The two first perspective images are images generated based on different viewpoints. When a user designates regions R41 and R42 on the first perspective images, the label applicator 106 determines each of the first three-dimensional regions determined by the region R41 and R42. The label applicator 106 applies a label to a region in which two first three-dimensional regions overlap each other in the three-dimensional volume data. Voxels on which the label is applied in the three-dimensional volume data are given the opacity by the three-dimensional image generator 137 to be expressed as an image which may be visualized in the three-dimensional image and displayed as a region R40 on which the label is applied in the three-dimensional image.

The user may designate at least one two-dimensional region on the first perspective images generated based on the three-dimensional volume data using the image processor 100C according to the fourth embodiment to set the region of interest (ROI) on the three-dimensional volume data. Moreover, a tissue which corresponds to a specific CT value in the region of interest set on the three-dimensional volume data may be made to be stereoscopic views to make it possible for the user to understand whether a suitable region of interest could be set or not.

According to the image processor of at least one embodiment as described above, a label applicator which determines a the first three-dimensional region based on a viewpoint for perspective projection to generate the first perspective image and the two-dimensional region designated on the first perspective image, and the label applicator applies a label on the first three-dimensional region as a region of interest (ROI) to make it possible to easily set the ROI in the three-dimensional volume data.

Further, each of the above image processors may be implemented by a general semiconductor integrated circuit, or a customizable electronic circuit such as an FPGA (field programmable gate array). Also each of the above image processors may be implemented by a processor and a memory that stores processor-executable instructions that, when executed by the processor, to cause the processor to perform the above-described acts or operations for the above-described image processing.

In other cases, one or more programs for the image processor of each of the above embodiments to perform the above-described acts or operations for the above-described image processing may be stored in a computer-readable recording medium, so that a computer system can read and execute the program stored in the computer-readable recording medium, thereby performing the positioning process.

Further, the "computer-readable storage medium" may include any non-transitory computer-readable storage mediums such as a storage device, such as a portable medium, for example, a flexible disk, a magneto optical disk, a ROM, or a CD-ROM, or a hard disk built in a computer system. Moreover, the computer-readable storage medium may also include a medium that temporarily stores a program, such as a volatile memory included in a computer system which serves as a server or client when the program is transmitted via a network such as the Internet, or a communication line such as a telephone line.

Additionally, the above program may be transmitted from a computer system storing that program in a storage device thereof to another computer system via a transmission medium or by carrier waves passing through a transmission medium. The "transmission medium" that transmits the program may include a medium having a function of transmitting information, such as a communication network, for example, the Internet, or a communication line, for example, a telephone line. Further, the above program may include a differential program in combination with the program already stored in the computer system.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processor, comprising:
   one or more memories that store one or more software components; and
   one or more processors configured to execute the one or more software components to perform at least:
      acquiring at least one two-dimensional region designated on at least one first perspective image generated from three-dimensional volume data of a target; and
      applying a label on at least one first three-dimensional region, wherein the at least one first three-dimensional region is a part of a second three-dimensional region, the second three-dimensional region is defined by the at least one two-dimensional region, a point and a surface which is defined by a set of straight line segments between the point and the boundary of the two-dimensional region, wherein
   the first three-dimensional region is defined to be a first overlapping region where the three-dimensional volume data and the second three-dimensional region overlap each other, and the at least one first perspective image is aligned with images acquired by capturing the target at a time different from a time at which the three-dimensional volume data of the target is obtained, based on the three-dimensional region with the label applied.

2. The processor as claimed in claim 1, wherein the point is a viewpoint for perspective projection to generate the first perspective image.

3. The processor as claimed in claim 2, wherein the at least one first perspective image includes a plurality of first perspective images, and the one or more processors are further configured to perform generating the plurality of first perspective images from the three-dimensional volume data using different viewpoints for perspective projection.

4. The processor as claimed in claim 3, wherein the one or more processors are further configured to
perform generating a first one of the first perspective image, the first one including a perspective projection of the at least one first three-dimensional region, and
perform making the perspective projection from a first one of the viewpoints to generate the perspective projection on the first one of the first perspective image, the first one of the viewpoints is different from a second one of the viewpoints for a second one of the first perspective image on which the at least one two-dimensional region is designated.

5. The processor as claimed in claim 4, further comprising:
a display device that displays the first one of the first perspective image.

6. The processor as claimed in claim 1, wherein
the at least one two-dimensional region is a plurality of two-dimensional regions,
the one or more processors are further configured to perform calculating the first three-dimensional region for each of the plurality of two-dimensional regions, and applying the label on a second overlapping region where the first three-dimensional regions overlap each other.

7. The processor as claimed in claim 1, wherein,
the one or more processors are further configured to perform applying the label on a set of voxels having voxel values in a range of voxel value, the set of voxels is in the first three-dimensional region.

8. The processor as claimed in claim 1, wherein,
the at least one two-dimensional region includes plural sets of the two-dimensional regions,
the one or more processors are further configured to perform calculating the first three-dimensional region for each two-dimensional region of the plural sets of the two-dimensional regions, and
perform applying a respective one of the labels on a second overlapping region where the first three-dimensional regions of each set of the two-dimensional regions overlap each other.

9. The processor as claimed in claim 8, wherein
the respective one of the labels is a respectively different one of the labels.

10. The processor as claimed in claim 1, wherein the one or more processors are further configured to perform
comparing the first perspective image with a second perspective image, the second perspective image being acquired with a radiographic imaging apparatus for capturing the target, and
generating the first perspective image from the three-dimensional volume data that includes the at least one first three-dimensional region.

11. The processor as claimed in claim 1, wherein the one or more processors are further configured to perform
calculating a dose distribution for radiation treatment, based on the three-dimensional volume data.

12. The processor as claimed in claim 1, wherein the one or more processors are futher configured to perform
generating a three-dimensional image of the at least one first three-dimensional region.

13. The processor according to claim 12, further comprising:
a bed that includes a movable mount for the target; and
a treatment apparatus for irradiating the target with radiation,
wherein the control apparatus, based on the difference in position, controls the movable mount for irradiation to the target.

14. The processor as claimed in claim 1, wherein the one or more processors are configured to further perform comparing the images with at least one third perspective image generated from the three-dimensional volume data including the three-dimensional region with the label applied, the one or more processors are configured to further perform aligning the at least one third perspective image with the images to calculate a difference in position of the target between when the three-dimensional volume data is acquired and when the images are acquired by capturing the target, the one or more processors are configured to further perform supplying the difference in position to a bed including a movable mount for the target to move the target.

15. An image processing method comprising:
acquiring, by a computer, at least one two-dimensional region designated on at least one first perspective image generated from three-dimensional volume data of a target; and
applying, by the computer, a label on at least one first three-dimensional region, wherein the at least one first three-dimensional region is a part of a second three-dimensional region, the second three-dimensional region is defined by the at least one two-dimensional region, a point and a surface which is defined by a set of straight line segments between the point and the boundary of the two-dimensional region, wherein
the first three-dimensional region is defined to be an overlapping region where the three-dimensional volume data and the second three-dimensional region overlap each other, and
the at least one first perspective image is aligned with images acquired by capturing the target at a time different from a time at which the three-dimensional volume data of the target is obtained, based on the three-dimensional region with the label applied.

16. A treatment system, comprising:
a radiographic imaging apparatus,
an image processor,
a planning apparatus that stores a three-dimensional volume data of a target and a treatment plan; and
a control apparatus,
wherein the image processor comprises:
one or more memories that store one or more software components:
one or more hardware processors configured to execute the one or more software components to perform at least:
acquiring at least one two-dimensional region designated on the at least one first perspective image generated from the three-dimensional volume data; and applying a label on at least one first three-dimensional region, wherein the at least one first three-dimensional region is a part of a second three-dimensional region, the second three-dimensional region is defined by the at least one two-dimensional region, a point and a surface which is defined by a set of straight line segments between the point and the boundary of the two-dimensional region, wherein the first three-dimensional region is defined to be an overlapping region where the three-dimensional volume data and the second three-dimensional region overlap each other, the radiographic imaging apparatus captures at least one second perspective images of the target, and the control apparatus generates at least one third perspective image from the three-dimensional volume data with the label applied, and the control apparatus performs an image comparison between the at least one second perspective image and the at least one third perspective image and, the control apparatus calculates a difference in position of the target between when the three-dimensional volume data, which is used for establishing the treatment plan, is generated by a device for computed tomography and when the at least one second perspective image is captured by the radiographic imaging apparatus.

17. The system according to claim 16, further comprising:
a bed that includes a movable mount for the target; and
a treatment apparatus for irradiating the target with radiation,
wherein the control apparatus, based on the difference in position, controls the movable mount for irradiation to the target.

* * * * *